(12) United States Patent
Katterbauer et al.

(10) Patent No.: US 12,258,858 B2
(45) Date of Patent: Mar. 25, 2025

(54) CONTROL SYSTEMS AND METHODS FOR ROCK CUTTINGS IDENTIFICATION

(71) Applicant: Saudi Arabian Oil Company, Dhahran (SA)

(72) Inventors: Klemens Katterbauer, Dhahran (SA); Alberto F. Marsala, Venice (IT); Nouf M. Jabri, Dammam (SA); Vera Solovyeva, Moscow (RU)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/552,775

(22) PCT Filed: Apr. 1, 2021

(86) PCT No.: PCT/RU2021/000139
§ 371 (c)(1),
(2) Date: Sep. 27, 2023

(87) PCT Pub. No.: WO2022/211659
PCT Pub. Date: Oct. 6, 2022

(65) Prior Publication Data
US 2024/0167381 A1 May 23, 2024

(51) Int. Cl.
*E21B 49/00* (2006.01)
*B82Y 15/00* (2011.01)
(Continued)

(52) U.S. Cl.
CPC ............ *E21B 49/005* (2013.01); *B82Y 15/00* (2013.01); *E21B 21/065* (2013.01); *E21B 47/04* (2013.01);
(Continued)

(58) Field of Classification Search
CPC ....... E21B 47/002; E21B 47/04; E21B 21/065
See application file for complete search history.

(56) References Cited

U.S. PATENT DOCUMENTS 7,937,222 B2   5/2011   Donadille et al.
8,627,902 B2   1/2014   Hammer
(Continued)

FOREIGN PATENT DOCUMENTS

CA   2851237   5/2013
GB   2489714   10/2012
(Continued)

OTHER PUBLICATIONS

Poitzsch et al., "Nanoparticle Tags for Improved Depth Correlation," IPTC-19785, International Petroleum Technology Conference (IPTC), IPTC Conference 2020, 2 pages (abstract only).
(Continued)

*Primary Examiner* — Kristyn A Hall
(74) *Attorney, Agent, or Firm* — Fish & Richardson P.C.

(57) ABSTRACT

Techniques for correlating a depth of drill bit cuttings include circulating a drilling fluid into a wellbore during a drilling process to form the wellbore in a subterranean formation; circulating a portion of uniquely identifiable particles from a container into the drilling fluid during the drilling process; circulating a return drilling fluid that includes the drilling fluid, cuttings from the subterranean formation, and the uniquely identifiable particles; separating the drilling fluid from the cuttings from the subterranean formation and the uniquely identifiable particles; capturing at least one image of the separated cuttings and the uniquely identifiable particles; and determining, based on the image, a depth of the subterranean formation.

25 Claims, 6 Drawing Sheets

(51) Int. Cl.
*E21B 21/06* (2006.01)
*E21B 47/04* (2012.01)
*G01N 33/28* (2006.01)
*G06T 7/70* (2017.01)
*G06V 10/70* (2022.01)

(52) U.S. Cl.
CPC ........... *G01N 33/2882* (2013.01); *G06T 7/70* (2017.01); *G06V 10/70* (2022.01)

(56) References Cited

U.S. PATENT DOCUMENTS

| | | |
|---|---|---|
| 8,680,866 B2 | 3/2014 | Marsala et al. |
| 8,812,237 B2 | 8/2014 | Wilt et al. |
| 9,260,957 B2 | 2/2016 | Commarieu et al. |
| 9,366,099 B2 | 6/2016 | Ly |
| 9,405,033 B2 | 8/2016 | Marsala et al. |
| 9,611,736 B2 | 4/2017 | Marsala et al. |
| 9,651,700 B2 | 5/2017 | Marsala et al. |
| 9,696,450 B2 | 7/2017 | Marsala et al. |
| 9,983,328 B2 | 5/2018 | Marsala et al. |
| 10,125,586 B2 | 11/2018 | Balan et al. |
| 10,132,952 B2 | 11/2018 | Marsala et al. |
| 10,145,975 B2 | 12/2018 | Marsala et al. |
| 10,156,654 B2 | 12/2018 | Marsala et al. |
| 10,267,943 B2 | 4/2019 | Marsala et al. |
| 10,377,938 B2 | 8/2019 | Sarkar et al. |
| 10,408,045 B2 | 9/2019 | Cox |
| 10,488,387 B2 | 11/2019 | Waid |
| 10,570,716 B2 | 2/2020 | Balan et al. |
| 10,612,360 B2 | 4/2020 | Al-Qasim et al. |
| 10,677,034 B2 | 6/2020 | Balan et al. |
| 10,677,035 B2 | 6/2020 | Balan et al. |
| 10,808,529 B2 | 10/2020 | Ow et al. |
| 11,427,742 B2 | 8/2022 | AlJabri et al. |
| 2004/0108110 A1 | 6/2004 | Zupanick et al. |
| 2005/0252286 A1 | 11/2005 | Ibrahim et al. |
| 2009/0087911 A1 | 4/2009 | Rogerio |
| 2010/0132448 A1 | 6/2010 | Donadille et al. |
| 2010/0198519 A1 | 8/2010 | Wilt et al. |
| 2012/0062886 A1 | 3/2012 | Piotti et al. |
| 2012/0178653 A1 | 7/2012 | McClung, III |
| 2012/0268135 A1 | 10/2012 | Marsala et al. |
| 2012/0325465 A1* | 12/2012 | Hammer ................. E21B 21/08 166/64 |
| 2014/0203810 A1 | 7/2014 | Marsala et al. |
| 2014/0203811 A1 | 7/2014 | Marsala et al. |
| 2014/0319379 A1 | 10/2014 | Manian |
| 2014/0361777 A1 | 12/2014 | Marsala et al. |
| 2015/0061683 A1 | 3/2015 | Marsala et al. |
| 2015/0061684 A1 | 3/2015 | Marsala et al. |
| 2015/0132543 A1 | 5/2015 | Nouzille et al. |
| 2015/0232748 A1* | 8/2015 | Kanj ....................... E21B 49/00 977/774 |
| 2016/0291194 A1 | 10/2016 | Marsala et al. |
| 2017/0059668 A1 | 3/2017 | Chang et al. |
| 2017/0351000 A1 | 12/2017 | Marsala et al. |
| 2018/0066515 A1 | 3/2018 | Marsala et al. |
| 2018/0171782 A1 | 6/2018 | Cox et al. |
| 2018/0275306 A1 | 9/2018 | Marsala et al. |
| 2018/0298752 A1 | 10/2018 | Balan et al. |
| 2018/0347349 A1 | 12/2018 | Marsala |
| 2019/0003291 A1 | 1/2019 | Balan et al. |
| 2019/0003292 A1 | 1/2019 | Balan et al. |
| 2019/0011593 A1 | 1/2019 | Marsala et al. |
| 2019/0169975 A1 | 6/2019 | Al-Qasim et al. |
| 2019/0368336 A1 | 12/2019 | Hammond et al. |
| 2019/0391034 A1 | 12/2019 | Al Jabri |
| 2020/0030777 A1 | 1/2020 | Al-Jabri et al. |
| 2020/0031738 A1 | 1/2020 | Al-Jabri et al. |
| 2020/0032148 A1 | 1/2020 | Al-Jabri et al. |
| 2020/0116019 A1 | 4/2020 | Ow et al. |
| 2020/0208513 A1 | 7/2020 | Al-Qasim et al. |
| 2021/0254449 A1* | 8/2021 | Wei ....................... E21B 47/002 |
| 2021/0319257 A1* | 10/2021 | Francois .............. G01N 15/088 |
| 2022/0056329 A1 | 2/2022 | Al-Jabri et al. |

FOREIGN PATENT DOCUMENTS

| | | |
|---|---|---|
| WO | WO 2012115717 | 8/2012 |
| WO | WO 2014051789 | 4/2014 |
| WO | WO 2014060562 | 4/2014 |
| WO | WO 2014207075 | 12/2014 |
| WO | WO 2017136641 | 8/2017 |
| WO | WO 2018085504 | 5/2018 |
| WO | WO 2018234431 | 12/2018 |
| WO | WO 2019212670 | 11/2019 |
| WO | WO 2020019367 | 1/2020 |
| WO | WO-2020019367 A1 * | 1/2020 ............. E21B 47/04 |

OTHER PUBLICATIONS

Allard et al., "Core-shell type dually fluorescent polymer nanoparticles for ratiometric pH-sensing," J. Polym. Sci., Part A: Polym. Chem., 2008, 46(18):6206-6213.

Behnke et al., "Encapsulation of Hydrophobic Dyes in Polystyrene Micro- and Nanoparticles via Swelling Procedures," J. Fluoresc., 2011, 21(3):937-944.

Deschamps et al., "Drilling to the Extreme: the Micro-Coring Bit Concept," IADC/SPE 115187, presented at the IADC/SPE Asia Pacific Drilling Technology Conference and Exhibition, Aug. 25-27, 2008, 12 pages.

Desmette et al., "Drilling Hard and Abrasive Rock Efficiently, or Generating Quality Cuttings? You No Longer Have to Choose . . . ," SPE 116554, Society of Petroleum Engineers, 2008 SPE Annual Technical Conference and Exhibition, Sep. 21-24, 2008, 19 pages.

Georgi, et al., "Advances in Cuttings Collection and Analysis," SPWLA 34th Annual Logging Symposium, Jun. 13-16, 1993, 20 pages.

Musyanovych et al., "Preparation of Biodegradable Polymer Nanoparticles by Miniemulsion Technique and Their Cell Interactions," Macromolecular Bioscience, Feb. 2008, 8(2):127-139.

Reisch et al., "Fluorescent Polymer Nanoparticles Based on Dyes: Seeking Brighter Tools for Bioimaging," Small, Apr. 2016, 12(15):1968-1992, 48 pages.

Santarelli et al., "Formation Evaluation From Logging on Cuttings," SPE Reservoir Evaluation and Engineering, presented at the 1996 SPE Permian Basin Oil and Gas Recovery Conference, Mar. 27-29, 1996, 7 pages.

Vollrath et al., "Fluorescence imaging of cancer tissue based on metal-free polymeric nanoparticles—a review," J. Mater. Chem. B, Mar. 2013, 1(15):1994-2007.

PCT International Search Report and Written Opinion in International Appln. No. PCT/US2021/046916, mailed on Nov. 17, 2021, 14 pages.

PCT International Preliminary Report on Patentability in International Appln. No. PCT/US2021/046916, mailed on Mar. 9, 2023, 14 pages.

PCT International Search Report and Written Opinion in International Appln. No. PCT/RU2021/000139, dated Nov. 25, 2021, 11 pages.

* cited by examiner

300

305

CONTROL SYSTEMS AND METHODS FOR ROCK CUTTINGS IDENTIFICATION

CROSS-REFERENCE TO RELATED APPLICATIONS

This application is a U.S. National Phase Application under 35 U.S.C. § 371 and claims the benefit of priority to International Application Serial No. PCT/RU2021/000139, filed Apr. 1, 2021, the contents of which are hereby incorporated by reference.

TECHNICAL FIELD

This disclosure relates to methods and systems for identifying cuttings of rock from drilling fluids.

BACKGROUND

The determination of depth origins of cuttings returned within a drilling fluid to a terranean surface is challenging and can delay advanced drilling fluid logging of achieving a quality desired or necessary for enhanced geo-steering, well placement, and improvement of a petrophysical analysis. The quality of conventional practice to determine the depth origins is usually poor with an uncertainty of, for example, plus-or-minus 15 feet depth. Conventional depth origins determination typically depends on wellbore mud hydraulics, hole cleaning, accurate knowledge of the return-trip lag time up the annulus, challenges in the discrimination of wellbore collapses (or cavings) and of potentially lagged cuttings during their trip to the surface. This is even more challenging in long horizontal sections of a wellbore being drilled, where gravitational debris accumulation, hydraulics, and hole cleaning can be more problematic. Additionally, the depth origins uncertainties can reach, for example, plus-or-minus 20 feet if an trip of cuttings lasts about 30 minutes. Also, potentially inaccurate labeling of collected cuttings can increase these errors.

SUMMARY

This disclosure describes implementations of a depth correlation system for a drilling process. In some aspects, the depth correlation system includes a control system (for example, artificial intelligence based control system) to automatically detect uniquely identifiable particles, such as nanoparticles of unique fluorescent spectra, attached to drill cuttings to determine a depth of a subterranean formation from which the cuttings were drilled.

In a general implementation, a drilling system includes a drilling fluid sub-assembly that includes one or more drilling fluid pumps configured to circulate a drilling fluid into a wellbore during a drilling process to form the wellbore in one or more subterranean formations; a cuttings collection sub-assembly configured to collect a plurality of cuttings from the subterranean formation from the drilling fluid circulated from the wellbore during the drilling process; a tagging sub-assembly that includes a plurality of containers, each of the containers configured to enclose a plurality of uniquely identifiable particles; and a control system communicably coupled to the cuttings collection sub-assembly and the tagging sub-assembly. The control system is configured to perform operations including controlling the tagging sub-assembly to circulate a portion of the plurality of uniquely identifiable particles from one of the plurality of containers into the drilling fluid during the drilling process; identifying at least one image from an image capture device of the cuttings collection sub-assembly, the image including a portion of cuttings from at least one of the one or more subterranean formations and at least one of the portion of the plurality of uniquely identifiable particles from one of the plurality of containers circulated into the drilling fluid during the drilling process; and determining, based on the image, a depth of the at least one of the one or more subterranean formations.

In an aspect combinable with the general implementation, the cuttings collection sub-assembly includes a shaker assembly configured to receive a mixture of the drilling fluid circulated from the wellbore during the drilling process, the portion of cuttings from at least one of the one or more subterranean formations, and the at least one of the portion of the plurality of uniquely identifiable particles from one of the plurality of containers and separate the drilling fluid from the portion of cuttings and the at least one of the portion of the plurality of uniquely identifiable particles.

In another aspect combinable with any one of the previous aspects, each plurality of uniquely identifiable particles include a plurality of uniquely identifiable nanoparticles.

In another aspect combinable with any one of the previous aspects, each plurality of uniquely identifiable nanoparticles includes a unique fluorescent spectra.

In another aspect combinable with any one of the previous aspects, the operation of controlling the tagging sub-assembly to circulate the portion of the plurality of uniquely identifiable particles from one of the plurality of containers into the drilling fluid during the drilling process includes controlling a valve of the one of the plurality of containers to adjust toward or to an open position to circulate the portion of the plurality of uniquely identifiable particles from the one of the plurality of containers into the drilling fluid during the drilling process.

In another aspect combinable with any one of the previous aspects, the control system is configured to perform operations further including determining, based on the image, an amount of the portion of the plurality of uniquely identifiable particles from one of the plurality of containers in the portion of cuttings from at least one of the one or more subterranean formations; comparing the determined amount of the portion of the plurality of uniquely identifiable particles with an expected amount of the portion of the plurality of uniquely identifiable particles; and based on the determined amount being less than the expected amount, controlling the tagging sub-assembly to circulate an increased portion of the plurality of uniquely identifiable particles from one of the plurality of containers into the drilling fluid during the drilling process.

In another aspect combinable with any one of the previous aspects, the expected amount of the portion of the plurality of uniquely identifiable particles is based at least in part on one or more parameters of the drilling process.

In another aspect combinable with any one of the previous aspects, the operation of determining, based on the image, the depth of the at least one of the one or more subterranean formations includes identifying a drilling depth of the drilling process; identifying a time of the circulation of the portion of the plurality of uniquely identifiable particles from one of the plurality of containers into the drilling fluid during the drilling process; and correlating the depth of the at least one of the one or more subterranean formations based on the drilling depth and the time.

In another aspect combinable with any one of the previous aspects, the control system is configured to perform operations further including controlling the tagging sub-assembly to circulate a portion of the plurality of uniquely identifiable particles from another one of the plurality of containers into the drilling fluid during the drilling process; identifying at least another image from the image capture device of the cuttings collection sub-assembly, the another image including a portion of cuttings from at least another one of the one or more subterranean formations and at least one of the portion of the plurality of uniquely identifiable particles from the another one of the plurality of containers circulated into the drilling fluid during the drilling process; and determining, based on the another image, a depth of the at least another one of the one or more subterranean formations.

In another aspect combinable with any one of the previous aspects, the control system includes an artificial intelligence controller that includes at least one neural network.

In another general implementation, a method includes circulating a drilling fluid into a wellbore during a drilling process to form the wellbore in one or more subterranean formations; circulating a portion of uniquely identifiable particles from one of a plurality of containers into the drilling fluid during the drilling process; circulating a return drilling fluid from the wellbore during the drilling process, the return drilling fluid including the drilling fluid, a plurality of cuttings from at least one of the one or more subterranean formations, and at least one of the portion of the uniquely identifiable particles; separating the drilling fluid from the plurality of cuttings from at least one of the one or more subterranean formations and the at least one of the portion of the uniquely identifiable particles; capturing at least one image of the separated plurality of cuttings and the at least one of the portion of the uniquely identifiable particles; and determining, based on the image, a depth of the at least one of the one or more subterranean formations.

In an aspect combinable with the general implementation, the plurality of uniquely identifiable particles are separated into groups of uniquely identifiable particles, each group of uniquely identifiable particles enclosed in one of the plurality of containers.

In another aspect combinable with any one of the previous aspects, each group of uniquely identifiable particles includes a group of uniquely identifiable nanoparticles.

In another aspect combinable with any one of the previous aspects, each group of uniquely identifiable nanoparticles includes a group of nanoparticles of a unique fluorescent spectra.

Another aspect combinable with any one of the previous aspects further includes opening a valve of the one of the plurality of containers to circulate the portion of uniquely identifiable particles from the one of the plurality of containers into the drilling fluid during the drilling process.

Another aspect combinable with any one of the previous aspects further includes determining, based on the image, an amount of the portion of the uniquely identifiable particles from the one of the plurality of containers in the portion of cuttings from at least one of the one or more subterranean formations; comparing the determined amount of the portion of the uniquely identifiable particles with an expected amount of the portion of the of uniquely identifiable particles; and based on the determined amount being less than the expected amount, circulating an increased portion of uniquely identifiable particles from the one of the plurality of containers into the drilling fluid during the drilling process.

In another aspect combinable with any one of the previous aspects, the expected amount of the portion of the uniquely identifiable particles is based at least in part on one or more parameters of the drilling process.

In another aspect combinable with any one of the previous aspects, determining, based on the image, the depth of the at least one of the one or more subterranean formations includes identifying a drilling depth of the drilling process; identifying a time of the circulation of the portion of the uniquely identifiable particles from the one of the plurality of containers into the drilling fluid during the drilling process; and correlating the depth of the at least one of the one or more subterranean formations based on the drilling depth and the time.

Another aspect combinable with any one of the previous aspects further includes circulating another portion of uniquely identifiable particles from another one of the plurality of containers into the drilling fluid during the drilling process; circulating the return drilling fluid from the wellbore during the drilling process, the return drilling fluid including the drilling fluid, a plurality of cuttings from at least another one of the one or more subterranean formations, and at least one of the another portion of the uniquely identifiable particles; separating the drilling fluid from the plurality of cuttings from the another one of the one or more subterranean formations and the at least one of the another portion of the uniquely identifiable particles; capturing at least another image of the separated plurality of cuttings and the at least one of the another portion of the uniquely identifiable particles; and determining, based on the another image, a depth of the at least another one of the one or more subterranean formations.

In another aspect combinable with any one of the previous aspects, determining, based on the image, the depth of the at least one of the one or more subterranean formations includes determining, based on the image, the depth of the at least one of the one or more subterranean formations with an artificial intelligence controller that includes at least one neural network.

In another general implementation, a computer-implemented method for determining a depth of a subterranean formation includes operating, with one or more hardware processors, a camera to capture a first plurality of images of a mixture of cuttings from a first subterranean formation and fluorescent nanoparticles attached to the cuttings from the first subterranean formation within a drilling fluid returned from a wellbore during a drilling process; determining, with the one or more hardware processors, a particular fluorescent spectra unique to the fluorescent nanoparticles attached to the cuttings from the first subterranean formation based on the first plurality of images; determining, with the one or more hardware processors, an arrival time of the fluorescent nanoparticles attached to the cuttings from the first subterranean formation at a drill bit of the drilling process; determining, with the one or more hardware processors, a depth of the drill bit at the determined arrival time; and based on the determined arrival time and depth of the drill bit, determining a depth of the first subterranean formation below a terranean surface.

An aspect combinable with the general implementation further includes operating, with one or more hardware processors, the camera to capture a second plurality of images of a mixture of cuttings from a second subterranean formation and fluorescent nanoparticles attached to the cuttings within the drilling fluid returned from the wellbore during the drilling process; determining, with the one or more hardware processors, a particular fluorescent spectra unique to the fluorescent nanoparticles attached to the cuttings from the second subterranean formation that is different than the particular fluorescent spectra unique to the fluorescent nanoparticles attached to the cuttings from the first subterranean formation based on the second plurality of images; determining, with the one or more hardware processors, another arrival time of the fluorescent nanoparticles attached to the cuttings from the second subterranean formation at the drill bit; determining, with the one or more hardware processors, another depth of the drill bit at the determined another arrival time; and based on the determined another arrival time and the another depth of the drill bit, determining a depth of the second subterranean formation below the terranean surface.

Another aspect combinable with any one of the previous aspects further includes distinguishing, with the one or more hardware processors, the cuttings from the first subterranean formation and the cuttings from the second subterranean formation based on a difference between the particular fluorescent spectra unique to the fluorescent nanoparticles attached to the cuttings from the first subterranean formation and the particular fluorescent spectra unique to the fluorescent nanoparticles attached to the cuttings from the second subterranean formation.

Another aspect combinable with any one of the previous aspects further includes determining, with the one or more hardware processors, a travel time of the fluorescent nanoparticles attached to the cuttings from the first subterranean formation from a release time to the arrival time of the fluorescent nanoparticles attached to the cuttings from the first subterranean formation at the drill bit.

Another aspect combinable with any one of the previous aspects further includes calculating, with the one or more hardware processors, the travel time based at least in part on a flow rate of the drilling fluid in the drilling process and one or more dimensions of the wellbore.

Implementations of a depth correlation system for a wellbore drilling process according to the present disclosure may include one or more of the following features. For example, the depth correlation system can correlate rock cuttings to their depth, and hence allow for more accurate interpretation of the cuttings in real time. As another example, the depth correlation system can provide an improved interpretation of reservoir zones. As a further example, the depth correlation system can assist drillers in planning drillings and improve geosteering. As another example, the depth correlation system can facilitate a forecast of potential rock types that may cause gas intrusion into the well, potentially endangering the operations. As a further example, the depth correlation system can utilize real-time images for a failure analysis and process optimization.

The details of one or more implementations of the subject matter described in this disclosure are set forth in the accompanying drawings and the description below. Other features, aspects, and advantages of the subject matter will become apparent from the description, the drawings, and the claims.

DETAILED DESCRIPTION

This disclosure describes implementations of a depth correlation system for a drilling process. In some aspects, the depth correlation system includes a control system (for example, artificial intelligence based control system) to automatically detect uniquely identifiable particles, such as nanoparticles of unique fluorescent spectra, attached to drill cuttings to determine a depth of a subterranean formation from which the cuttings were drilled.

Figure 1:
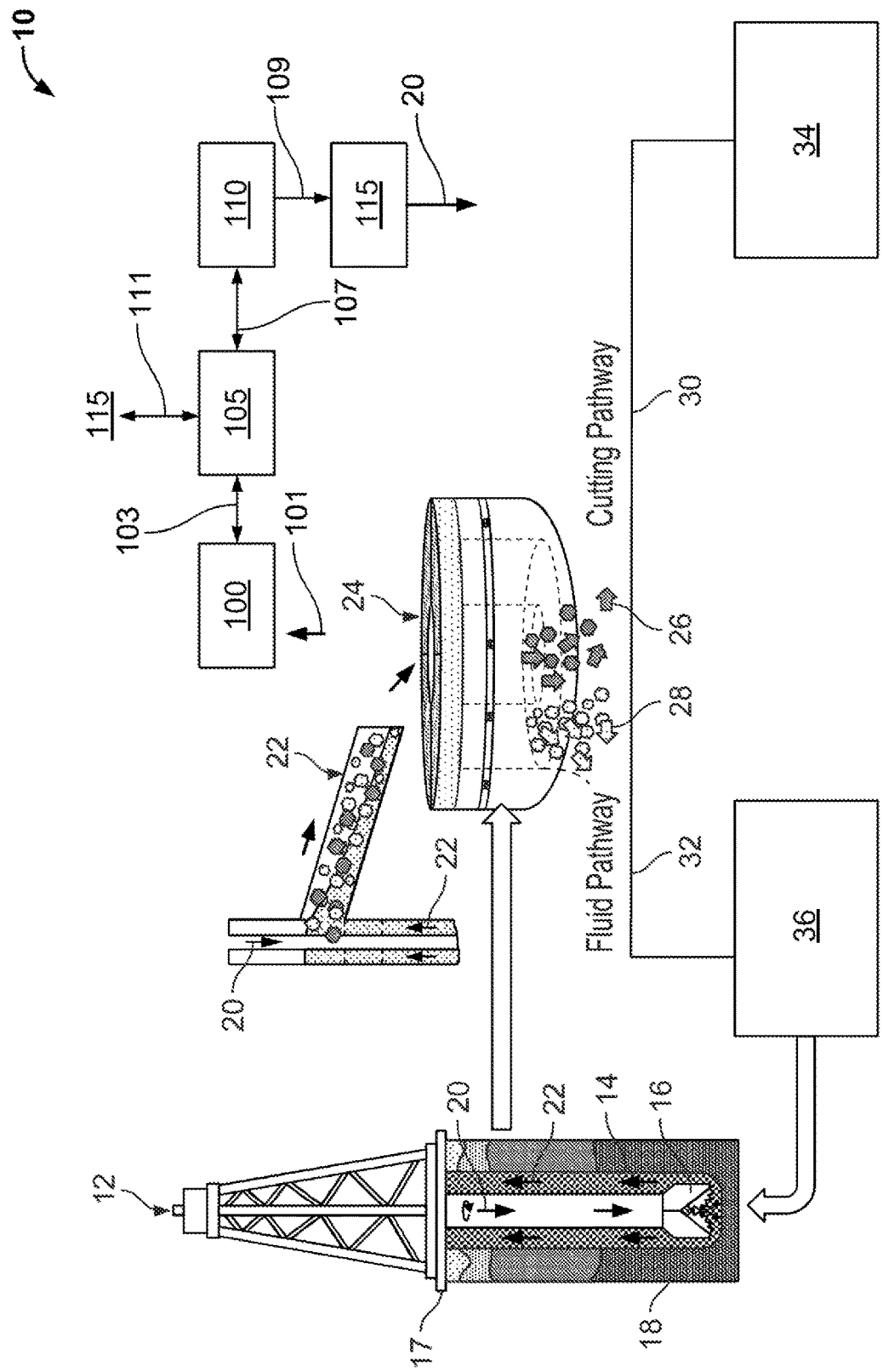
FIG. 1 is a schematic diagram of a wellbore drilling process that includes a depth correlation system according to the present disclosure.

FIG. 1 is a schematic diagram of wellbore drilling process 10 that includes a depth correlation system according to the present disclosure. Generally, the drilling process 10 represents a process in which a wellbore 14 is formed from a terranean surface 17 and through one or more subterranean formations 18 by a drilling rig 12. The drilling process 10, in this example, includes a drill bit 16 coupled to a downhole conveyance (for example, a tubular drill string, such as conventional or coiled tubing) that forms the wellbore 14 with a drilling fluid 20. The drilling fluid 20 is provided to the drill bit 16 by, for example, the downhole conveyance, and circulates through the drill bit 16 during drilling of the wellbore 14 in order to, for example, cool the drill bit 16 and removing cuttings from the subterranean formation 18 back to the surface 17. Thus, return drilling fluid 22 includes the drilling fluid 20 (for example, a water or foam and chemical mixture) as well as cuttings (for example, bits of rock cut from the formation 18 by the drill bit 16). Return drilling fluid 22, therefore, includes liquid 28 and cuttings 26 from the formation 18, which may be removed.

As explained in more detail herein, an example depth correlation system according to the present disclosure includes an image capture device 100 positioned to capture one or more images 101 (for example, still or video images in conventional light spectrums, infrared spectrums, or otherwise) of the cuttings from the return drilling fluid 22, as well as one or more fluorescent nanoparticles attached to the cutting that are added to the drilling fluid 20 by the depth correlation system. The images 101 are analyzed by a control system 105, which, based on the analysis, controls a nanoparticle release system 110 to control an introduction of one or more nanoparticles of unique fluorescent spectra into the drilling fluid 22 through a drilling fluid pumping system 115. Further, the control system 105 can determine a depth of a subterranean formation from which the cuttings originated during the drilling process 10 based on a particular, unique fluorescent spectra of the nanoparticles attached to such cuttings. In some aspects, the control system 105 can be networked (wired or wirelessly) with the other components of the depth correlation system of FIG. 1.

As shown in FIG. 1, the return drilling fluid 22 is circulated out of the wellbore 14 to a shaker screen system 24. The shaker screen system 24 separates the liquid 28 from the cuttings 26 of the return drilling fluid 22 with a screen that includes one or more screen sections. As shown in the example implementation of FIG. 1, the liquid 28 and the cuttings 26 are separated into two separate streams. The liquid 28 is circulated from the shaker screen system 24 in a fluid pathway 32 and into a mud tank 36. Generally, the mud tank 36 is used to hold the separated liquid 28 and provide the separated liquid 28 as a source of liquid for additional drilling fluid 20 (in other words, to recycle back into the drilling process 10 as drilling fluid 20). The cuttings 26 are circulated into a cuttings pathway 30 and into one or more waste pits 34. Generally, the waste pits 34 are pits or other enclosures that store the cuttings 26 for proper disposal.

In the example implementation of FIG. 1, the image capture device 100 is positioned above or adjacent the shaker screen system 24 to capture images 101 of the cuttings 26 and nanoparticles attached to the cuttings 26. The images 101 are communicated to the control system 105 through communications 103. In some aspects, the communications 103 include data sent from the image capture device 100 to the control system 105, such as the images 101, as well as instructions set from the control system 105 to the image capture device 100 (such as instructions to operate the image capture device 100 to capture the images 101).

In some aspects, the control system 105 comprises an artificial intelligence (AI) controller, as well as one or more device controllers (for example, valve controllers, pump controllers). The AI controller, in some example aspects, can utilize a two-step approach with two different neural networks. A first neural network performs image recognition on the cuttings 26 to discern the one or more unique fluorescent spectra of the nanoparticles attached to the cuttings 26. In some aspects, the first neural network comprises a deep convolutional neural network. A second neural network can set the control parameters for the nanoparticle release system 110, such as parameters for timing and amount of release of the one or more unique fluorescent spectra of nanoparticles into the drilling fluid 20. In some aspects, the second neural network can be a nonlinear autoregressive network model. In some aspects, the AI controller can be trained on a training data set of experimental data, simulation data, field test data, or a combination thereof.

In the illustrated implementation of FIG. 1, the control system 105 also communicates data 111 with the drilling fluid system 115. For example, the data 111 provided to the control system 105 (such as the AI controller) can include drilling fluid parameters, parameters of the wellbore 14, and other parameters of the drilling process 10. For example, drilling fluid and drilling process parameters can include properties (for example, viscosity, density, chemical make-up) of the drilling fluid 20, flow rate of the drilling fluid 20 into the wellbore 14 and out of the wellbore 14, flow rate of the drilling fluid 20 into a drill string, rate of penetration (ROP) of the drill bit 16, depth of the drill bit 16, and other information. Wellbore parameters can include, for example, dimensions of the wellbore such as diameter, casing dimensions, and dimensions of other tubulars within the wellbore (for example, liners).

The control system 105 is communicably coupled to the nanoparticle release system 110 to exchange data 107. In some aspects, the data 107 can include operational instructions provided by the control system 105, such as one or more device controllers according to an analysis of the AI controller, to one or more devices on the nanoparticle release system 110. In some aspects, the data 107 can also include feedback from the nanoparticle release system 110, such as regarding a position of the device.

Figure 2:
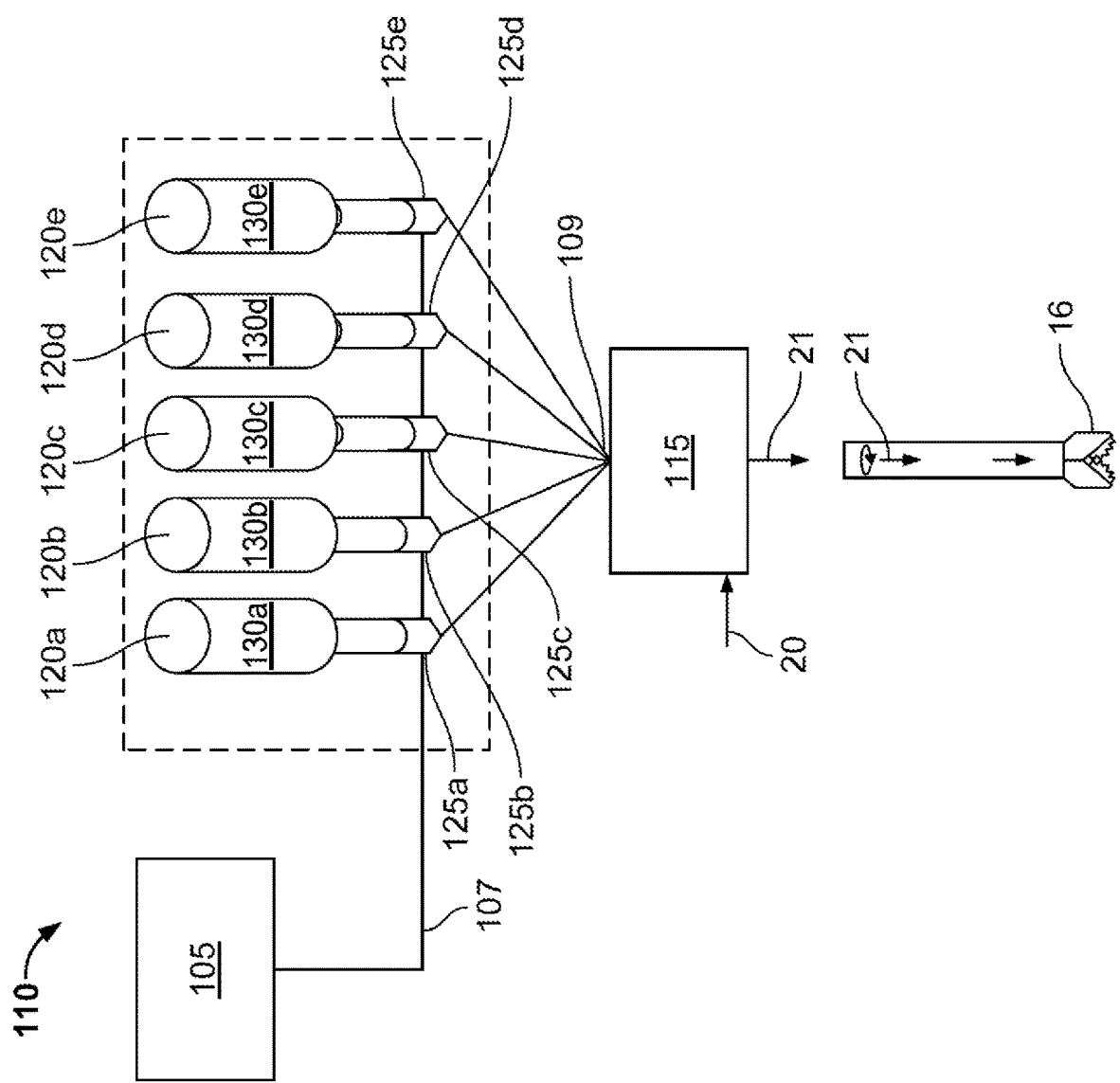
FIG. 2 is a schematic diagram of a portion of a depth correlation system according to the present disclosure.

Turning to FIG. 2, an example implementation of the nanoparticle release system 110 according to the present disclosure. As shown in FIG. 2, the nanoparticle release system 110 includes multiple nanoparticle canisters 120a-120e, each of which contains a batch of nanoparticles 130a-130f, respectively. In some aspects, each batch of nanoparticles 130a-130f is unique in its fluorescent spectra, and in some aspects, its chemical structure, as compared to the other batches of nanoparticles 130a-103f stored in canisters 120a-1250f. Thus, each batch of nanoparticles 130a-130e is visually (and in some aspects, chemically) distinguishable from every other batch of nanoparticles 130a-130f by the unique fluorescent spectra, which can be captured on the images 101 by the image capture device 100.

As shown in FIG. 2, each nanoparticle canister 120a-120f includes a release valve 125a-125f, respectively. Each release valve 125a-125f is controllable by the control system 105 (such as the device controllers) through data 107 (for example, commands from the control system 105) to selectively open or close the respective canister 120a-120f to release respective nanoparticles 130a-130f into the drilling fluid 20. In some aspects, each release valve 125a-125f can include or be coupled with a flow meter that measures a volumetric flow rate of nanoparticles released from the respective canister 120a-120f when the respective valve 125a-125f is opened. Once released, the nanoparticles from a particular canister 130a-135f is introduced through, for example, a manifold 109 as shown, into the drilling fluid pumping system 115, where the released nanoparticles are mixed within drilling fluid 20 and circulated into the wellbore 14 as fluid mixture 21, which represents a mixture of the drilling fluid 20 and at least a portion of one batch of uniquely colored (for example, unique fluorescent spectra) nanoparticles. Alternatively, the released nanoparticles can be introduced into the drilling fluid 20 (to form fluid mixture 21) between the drilling fluid pumping system 115 and an entry of the wellbore 14.

Figure 3A:
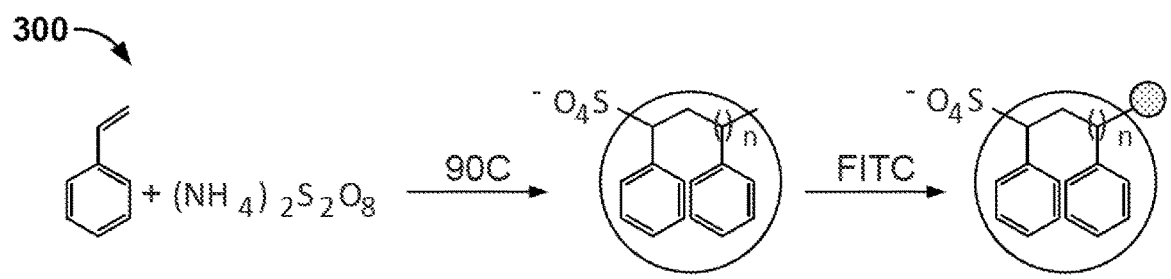
FIGS. 3A-3C are illustrations of example material additives for a drilling fluid used by a depth correlation system according to the present disclosure.
Figure 3B:
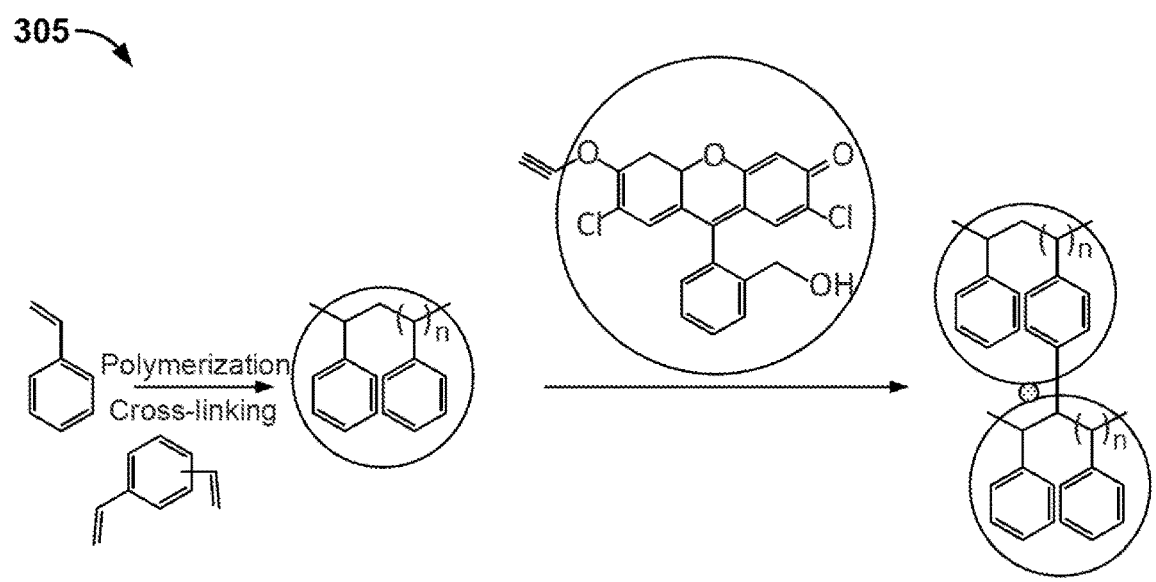
Figure 3C:
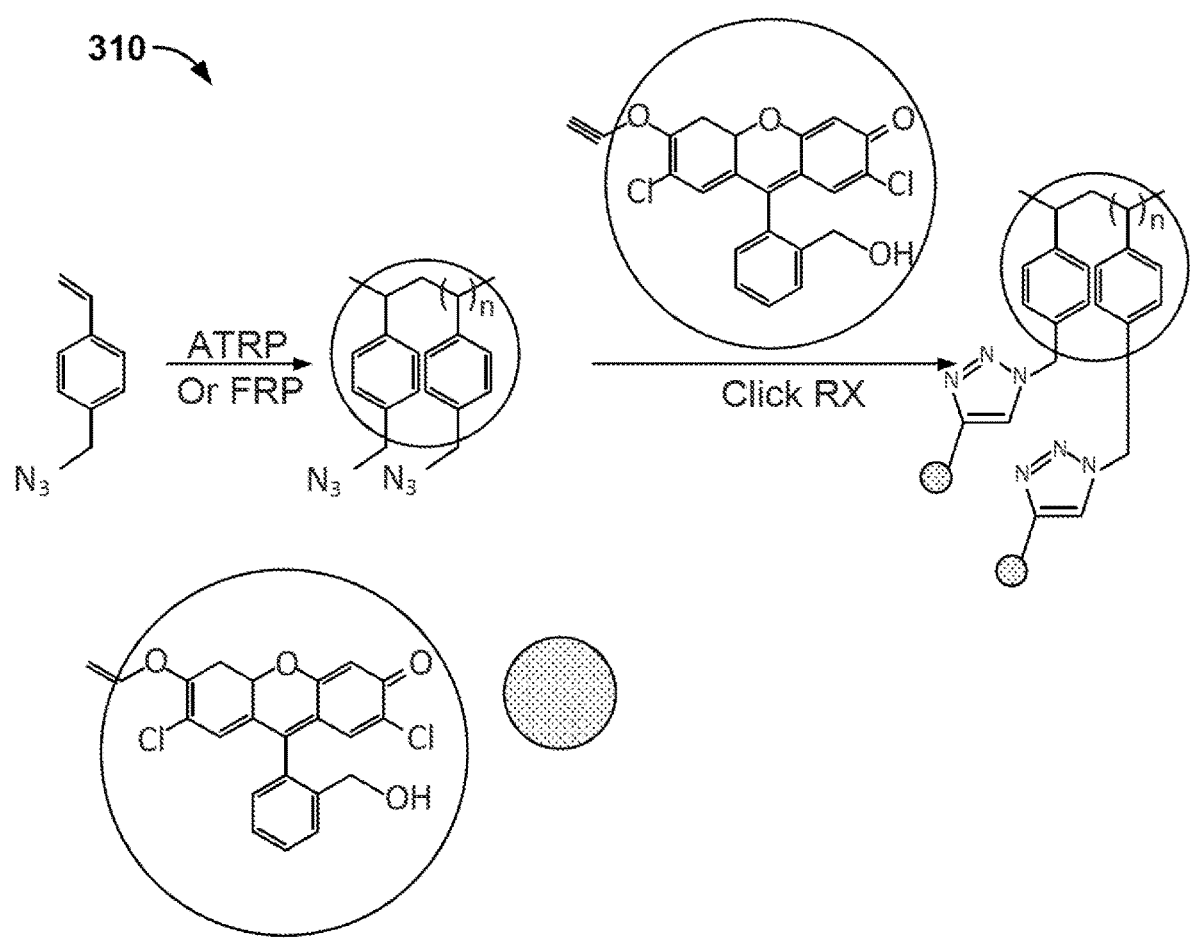

Turning briefly to FIGS. 3A-3C, example illustrations of a nanoparticle according to the present disclosure are shown. FIG. 3A shows a diagram 300 of a nanoparticle that is formed through a fluorescein isothiocyanate (FITC) labeled nanotag synthesis. For example, FIG. 3A shown an illustration of a styrene polymerization to form styrenic nanoparticles. An added dye can attach covalently to the styrenic nanoparticles surface. FITC is an example and the selection of dyes is not limited to FITC). Also, the styrene can be replaced by another monomer. The variety in the monomer and dyes can provide for a library of unique nanoparticles according to the present disclosure.

FIG. 3B shows a diagram 305 of nanoparticle that is formed through a fluorescent nanotag synthesis. For example, another technique to form a fluorescein labeled nanoparticle is by doping the fluorescein dye. FIG. 3B shows a radical polymerization of styrene and 1,4 divinylbenezne to produce a cross-linked network polymer (in other words, a crosslinking reaction). Subsequently, the dye can be doped into styrenic based cross-linked polymers net. The bond between the cross-linked network polymer and the dye, in some aspects, is uncovalent.

FIG. 3C shows a diagram 310 of a nanoparticle that is formed through a fluoresceine covalently labeled nanotag synthesis. This figure illustrates a dispersion copolymerization of styrene and vinylbenzyl azide to form a styrnic copolymer microsphere with a functional azide group ($N_3$). By using the click chemistry, a fluorescent dye can attach covalently to the $N_3$ on the surface of the microsphere to produce a unique nanoparticle according to the present disclosure.

Figure 4:
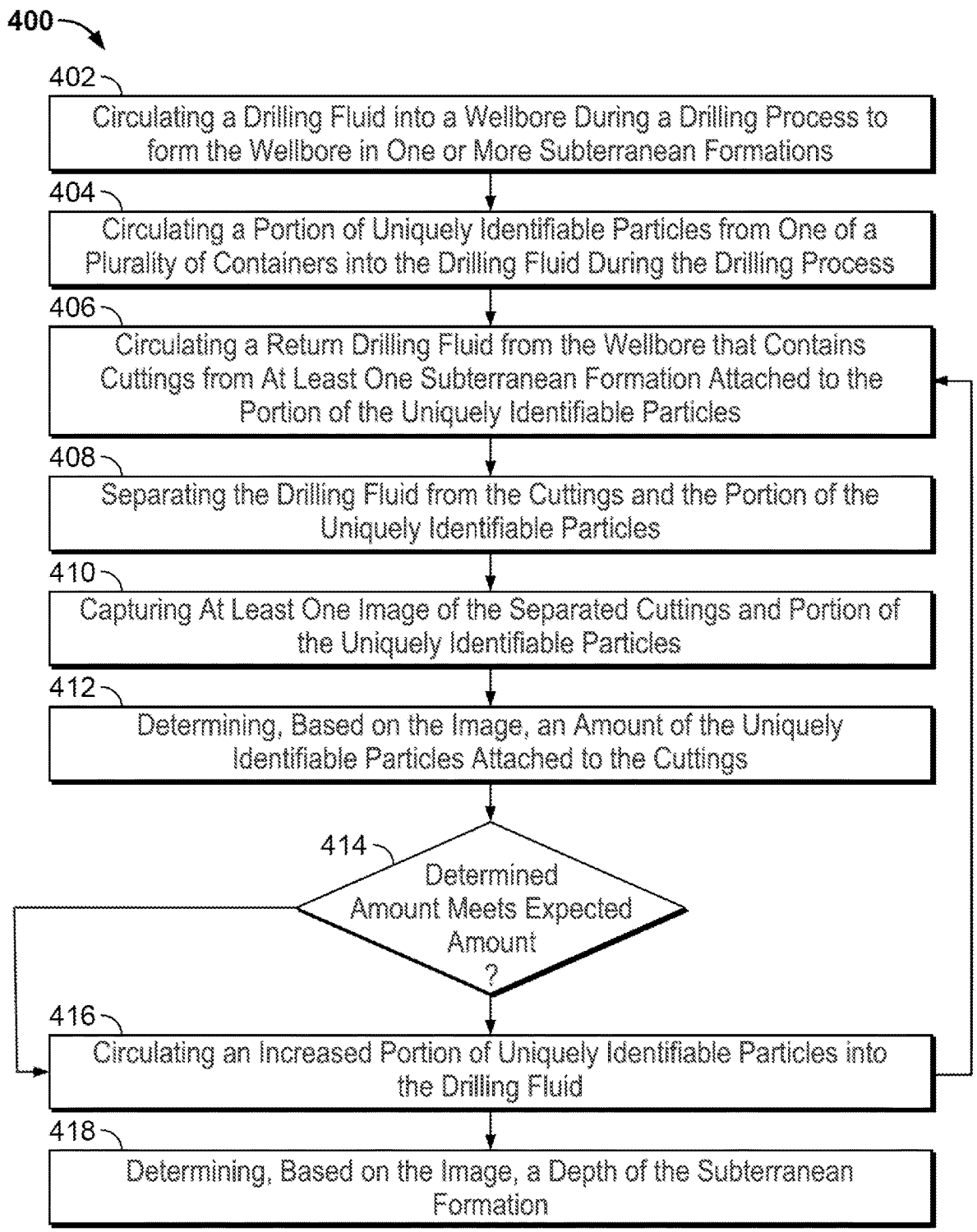
FIG. 4 is a flowchart that describes an example method for operating a depth correlation system for a wellbore drilling process according to the present disclosure.

FIG. 4 is a flowchart that describes an example method 400 for operating a depth correlation system for a wellbore drilling process. In some aspects, method 400 can be performed with the depth correlation system of drilling process 10 shown in FIG. 1. For example, all or portions of the method 400 can be performed with or by the control system 105 shown in FIG. 1. Method 400 can begin at step 402, which includes circulating a drilling fluid into a wellbore during a drilling process to form the wellbore in one or more subterranean formations. For example, drilling fluid 20 can be circulated into a drill string and through the drill bit 16 during the drilling process 10. The wellbore 14 can be formed with the drill bit 16 to and through subterranean formation 18. As part of the drilling process 10, cuttings from the subterranean formation 18 (and other formations at different depths under the terranean surface) are entrained in the drilling fluid 20 and returned in return drilling fluid 22. In some aspects, the drilling fluid pumping system 115 (which can be a conventional pumping system to circulate the drilling fluid 20) can operate independently or be operated by the control system 105).

Method 400 can continue at step 404, which includes circulating a portion of uniquely identifiable particles from one of a plurality of containers into the drilling fluid during the drilling process. For example, during the drilling process 10, the control system 105 can control the nanoparticle release system 110 to release uniquely identifiable nanoparticles stored in, for example, one of the canisters 120a-120f into the drilling fluid 20 (either at the drilling fluid pumping system 115 or elsewhere). The released nanoparticles can have a unique fluorescent spectra as compared to the batches of nanoparticles in the other canisters 120a-120f.

In some aspects, the control system 105 can provide a command 107 (for example, through a device controller of the system 105) to a release valve 125a-125f in order to release the uniquely identifiable nanoparticles into the drilling fluid 20 (to form the mixture 21 of the drilling fluid 20 and nanoparticles). The command 107, for instance, can open the release valve 125a-125f in order to open the respective canister 120a-120f.

In some aspects, step 404 can include a pulsed release of nanoparticles into the drilling fluid 20. For example, the control system 105, during the drilling process 10, can send commands 107 to the particular canister 120a-120f to provide a pulsed release of the nanoparticles into the drilling fluid 20 (for example, short time durations of release of nanoparticles interspersed with short time durations of non-release). In some aspects, each "release" pulse can release the same or similar amount or concentration of the uniquely identifiable nanoparticles. Alternatively, each release pulse can release a different amount or concentration of the uniquely identifiable nanoparticles. Once released into the drilling fluid 20, the mixture 21 of drilling fluid 20 and nanoparticles is circulated, for example, by the drilling fluid pumping system 115, into the drill string and through the drill bit 16 during the drilling process 10.

Method 400 can continue at step 406, which includes circulating a return drilling fluid from the wellbore that contains cuttings from at least one subterranean formation attached to the portion of the uniquely identifiable particles. For example, the return drilling fluid 22, which includes drilling fluid 20, cuttings 26, and nanoparticles attached to the cuttings 26. The return drilling fluid 22 can be circulated to a separation system, such as shaker screen system 24.

Method 400 can continue at step 408, which includes separating the drilling fluid from the cuttings and the portion of the uniquely identifiable particles. For example, as the return drilling fluid 22 is circulated into the shaker screen system 24, cuttings 26 with nanoparticles attached thereto can be separated (by one or more screens of the shaker screen system 24) from the drilling fluid 20. In some aspects, once separated, the cuttings 26 can be circulated into one or more waste pits 34, while the liquid 28 (which may consist of mainly drilling fluid 20) can be circulated back to a mud tank 36.

Method 400 can continue at step 410, which includes capturing at least one image of the separated cuttings and portion of the uniquely identifiable particles. For example, during the step of separation (step 408), one or more images 101 (still or video or both) of the separated cuttings 26 and attached nanoparticles can be captured by the image capture device 100 (for example, as controlled by the control system 105). In some aspects, the images 101 may be in a conventional (for example, human-detectable) wavelength spectra. In some aspects, the images 101 can be in a specific spectra to detect the unique fluorescent spectra of the nanoparticles.

Method 400 can continue at step 412, which includes determining, based on the image, an amount of the uniquely identifiable particles attached to the cuttings. For example, in some aspects, the control system 105 can determine an amount or concentration of the uniquely identifiable nanoparticles attached to the cuttings 26 based on the one or more images 101 captured in step 410. For example, the AI controller of the control system 105 can detect the amount or concentration of the nanoparticles based on, for example, an amount of the unique fluorescent spectra of the nanoparticles as compared to an amount of the cuttings 26 in the image 101.

Method 400 can continue at step 414, which includes a determination of whether the determined amount meets an expected amount. For example, the control system 105 (for example, the AI controller) can calculate or determine an expected amount (or concentration) of the uniquely identifiable nanoparticles based on an amount released in step 404. In some aspects, a flow meter (such as an ultrasonic flow meter) measures an amount of nanoparticles released from a particular canister 120a-120f. The flow meter can be part of, for example, the particular release valve 125a-125f. Through the flow meter measurement, the AI controller can determine or calculate how much nanoparticles have been circulated into the drilling fluid 20. The AI controller compares the determined amount from step 412 with the expected amount.

If the determination is no, then the AI controller determines that insufficient nanoparticles have been released (either in a single instance or pulsed) into the drilling fluid 20. The consequences of such insufficient amount, for example, can be that the images 101 are not adequate to make determinations relative to the cuttings 26. Based on a no determination, method 400 can continue at step 416, which includes circulating an increased portion of uniquely identifiable particles into the drilling fluid. For example, the control system 105 can provide additional commands 107 to further open the release valve 125a-125f of the respective canister 120a-120f to release more uniquely identifiable nanoparticles into the drilling fluid 20. Method 400 can continue from step 416 back to step 406.

If the determination in step 414 is yes, then method 400 can continue at step 418, which includes determining, based on the image, a depth of the subterranean formation. For example, the AI controller can utilize the captured images 101 that show the uniquely identifiable nanoparticles attached to the cuttings 26 along with one or more parameters of the drilling process 10 to determine a depth from which the cuttings 26 were removed from the subterranean formation (and thus, the subterranean formation itself). For example, the AI controller can determine an estimated arrival time of the released nanoparticles at the drill bit 16 based on a release time (for example, a time in which the nanoparticles were released from the nanoparticle release system 110 or in which the nanoparticles entered the drilling fluid 20) and drilling parameters, such as diameter of the wellbore 14 and drilling fluid flow rate. By determining the arrival time of the nanoparticles at the drill bit 16, the depth of the drill bit 16 at that arrival time can then be correlated by the AI controller. Since it can be assumed that the nanoparticles attach to the cuttings 26 from the subterranean formation at the depth of the drill bit 16, the depth of the cuttings 26 can be correlated with the depth of the drill bit 16 at the arrival time of the nanoparticles at the drill bit 16.

Method 400 can include other steps in addition to (or alternatively to) the illustrated steps. For example, in some aspects, the control system 105 can determine whether a particular one (or more) of the canisters 120a-120f is running low on nanoparticles in the canister 120a-120f (for example, less than 5% volume left). If such a determination is made, the control system 105 can provide, for example, an alert that indicates such a lack of nanoparticles in the particular canister or canisters 120a-120f. As another example, certain steps of method 400 can be repeated in series or parallel to introduce more than one batch of uniquely identifiable nanoparticles (in other words, nanoparticles with different fluorescent spectra) into the drilling fluid 20 at any given time. This can be done, for example, to identify several distinct depths correlated to different cuttings 26 by the nanoparticles of different spectra. For example, steps 404-418 can be repeated (in series or parallel) for more than one batch of nanoparticles from the canisters 120a-120f to correlate the depths of several batches of cuttings 26 in the return drilling fluid 22. As another example, one or more steps of method 400 are or can be implemented as a computer-implemented method by the control system 105. For example, steps 410-414 and 418 can be computer-implemented by the control system 105.

Figure 5:
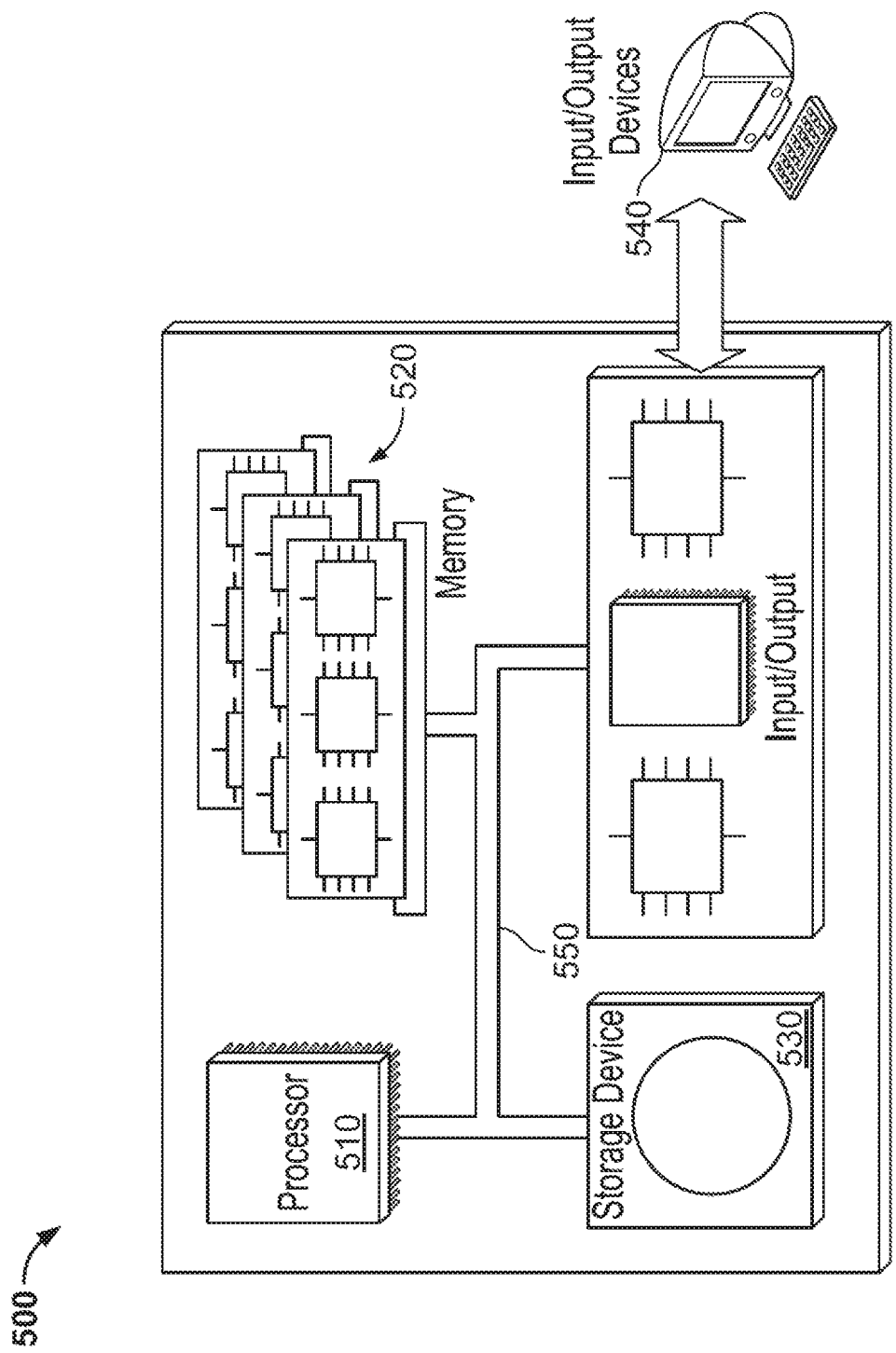
FIG. 5 is a schematic illustration of a control system for a depth correlation system according to the present disclosure.

FIG. 5 is a schematic diagram of a control system 500. The system 500 can be used for the operations described in association with any of the processes described previously, for example as or as part of the control system 105. The system 500 is intended to include various forms of digital computers, such as laptops, desktops, workstations, personal digital assistants, servers, blade servers, mainframes, and other appropriate computers. The system 500 can also include mobile devices, such as personal digital assistants, cellular telephones, smartphones, and other similar computing devices. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. The processor may be designed using any of a number of architectures. For example, the processor 510 may be a CISC (Complex Instruction Set Computers) processor, a RISC (Reduced Instruction Set Computer) processor, or a MISC (Minimal Instruction Set Computer) processor.

In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In one implementation, the memory 520 is a computer-readable medium. In one implementation, the memory 520 is a volatile memory unit. In another implementation, the memory 520 is a non-volatile memory unit.

The storage device 530 is capable of providing mass storage for the system 500. In one implementation, the storage device 530 is a computer-readable medium. In various different implementations, the storage device 530 may be a floppy disk device, a hard disk device, an optical disk device, or a tape device.

The input/output device 540 provides input/output operations for the system 500. In one implementation, the input/output device 540 includes a keyboard and/or pointing device. In another implementation, the input/output device 540 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Particular implementations of the subject matter have been described. Other implementations are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A drilling system, comprising:
    a drilling fluid sub-assembly that comprises one or more drilling fluid pumps configured to circulate a drilling fluid into a wellbore during a drilling process to form the wellbore in one or more subterranean formations;
    a cuttings collection sub-assembly configured to collect a plurality of cuttings from the subterranean formation from the drilling fluid circulated from the wellbore during the drilling process;
    a tagging sub-assembly that comprises a plurality of containers, each of the containers configured to enclose a plurality of uniquely identifiable particles; and
    a control system communicably coupled to the cuttings collection sub-assembly and the tagging sub-assembly and configured to perform operations comprising:
        controlling the tagging sub-assembly to circulate a portion of the plurality of uniquely identifiable particles from one of the plurality of containers into the drilling fluid during the drilling process;
        identifying at least one image from an image capture device of the cuttings collection sub-assembly, the image comprising a portion of cuttings from at least one of the one or more subterranean formations and at least one of the portion of the plurality of uniquely identifiable particles from one of the plurality of containers circulated into the drilling fluid during the drilling process;
        determining, based on the image, a depth of the at least one of the one or more subterranean formations;
        determining, based on the image, an amount of the portion of the plurality of uniquely identifiable particles from one of the plurality of containers in the portion of cuttings from at least one of the one or more subterranean formations;
        comparing the determined amount of the portion of the plurality of uniquely identifiable particles with an expected amount of the portion of the plurality of uniquely identifiable particles; and
        based on the determined amount being less than the expected amount, controlling the tagging sub-assembly to circulate an increased portion of the plurality of uniquely identifiable particles from one of the plurality of containers into the drilling fluid during the drilling process.

2. The drilling system of claim 1, wherein the cuttings collection sub-assembly comprises a shaker assembly configured to receive a mixture of the drilling fluid circulated from the wellbore during the drilling process, the portion of cuttings from at least one of the one or more subterranean formations, and the at least one of the portion of the plurality of uniquely identifiable particles from one of the plurality of containers and separate the drilling fluid from the portion of cuttings and the at least one of the portion of the plurality of uniquely identifiable particles.

3. The drilling system of claim 1, wherein each plurality of uniquely identifiable particles comprise a plurality of uniquely identifiable nanoparticles.

4. The drilling system of claim 3, wherein each plurality of uniquely identifiable nanoparticles comprises a unique fluorescent spectra.

5. The drilling system of claim 1, wherein the operation of controlling the tagging sub-assembly to circulate the portion of the plurality of uniquely identifiable particles from one of the plurality of containers into the drilling fluid during the drilling process comprises:
    controlling a valve of the one of the plurality of containers to adjust toward or to an open position to circulate the portion of the plurality of uniquely identifiable particles from the one of the plurality of containers into the drilling fluid during the drilling process.

6. The drilling system of claim 1, wherein the expected amount of the portion of the plurality of uniquely identifiable particles is based at least in part on one or more parameters of the drilling process.

7. The drilling system of claim 1, wherein the operation of determining, based on the image, the depth of the at least one of the one or more subterranean formations comprises:
  identifying a drilling depth of the drilling process;
  identifying a time of the circulation of the portion of the plurality of uniquely identifiable particles from one of the plurality of containers into the drilling fluid during the drilling process; and
  correlating the depth of the at least one of the one or more subterranean formations based on the drilling depth and the time.

8. The drilling system of claim 1, wherein the control system is configured to perform operations further comprising:
  controlling the tagging sub-assembly to circulate another portion of the plurality of uniquely identifiable particles from another one of the plurality of containers into the drilling fluid during the drilling process;
  identifying at least another image from the image capture device of the cuttings collection sub-assembly, the another image comprising a portion of cuttings from at least another one of the one or more subterranean formations and at least one of the another portion of the plurality of uniquely identifiable particles from the another one of the plurality of containers circulated into the drilling fluid during the drilling process; and
  determining, based on the another image, a depth of the at least another one of the one or more subterranean formations.

9. The drilling system of claim 1, wherein the control system comprises an artificial intelligence controller that comprises at least one neural network.

10. A method, comprising:
  circulating a drilling fluid into a wellbore during a drilling process to form the wellbore in one or more subterranean formations;
  circulating a portion of uniquely identifiable particles from one of a plurality of containers into the drilling fluid during the drilling process;
  circulating a return drilling fluid from the wellbore during the drilling process, the return drilling fluid comprising the drilling fluid, a plurality of cuttings from at least one of the one or more subterranean formations, and at least one of the portion of the uniquely identifiable particles;
  separating the drilling fluid from the plurality of cuttings from at least one of the one or more subterranean formations and the at least one of the portion of the uniquely identifiable particles;
  capturing at least one image of the separated plurality of cuttings and the at least one of the portion of the uniquely identifiable particles;
  determining, based on the image, a depth of the at least one of the one or more subterranean formations;
  determining, based on the image, an amount of the portion of the uniquely identifiable particles from the one of the plurality of containers in the portion of cuttings from at least one of the one or more subterranean formations;
  comparing the determined amount of the portion of the uniquely identifiable particles with an expected amount of the portion of the of uniquely identifiable particles; and
  based on the determined amount being less than the expected amount, circulating an increased portion of uniquely identifiable particles from the one of the plurality of containers into the drilling fluid during the drilling process.

11. The method of claim 10, wherein the plurality of uniquely identifiable particles are separated into groups of uniquely identifiable particles, each group of uniquely identifiable particles enclosed in one of the plurality of containers.

12. The method of claim 11, wherein each group of uniquely identifiable particles comprises a group of uniquely identifiable nanoparticles.

13. The method of claim 12, wherein each group of uniquely identifiable nanoparticles comprises a group of nanoparticles of a unique fluorescent spectra.

14. The method of claim 10, further comprising opening a valve of the one of the plurality of containers to circulate the portion of uniquely identifiable particles from the one of the plurality of containers into the drilling fluid during the drilling process.

15. The method of claim 10, wherein the expected amount of the portion of the uniquely identifiable particles is based at least in part on one or more parameters of the drilling process.

16. The method of claim 10, wherein determining, based on the image, the depth of the at least one of the one or more subterranean formations comprises:
  identifying a drilling depth of the drilling process;
  identifying a time of the circulation of the portion of the uniquely identifiable particles from the one of the plurality of containers into the drilling fluid during the drilling process; and
  correlating the depth of the at least one of the one or more subterranean formations based on the drilling depth and the time.

17. The method of claim 10, further comprising:
  circulating another portion of uniquely identifiable particles from another one of the plurality of containers into the drilling fluid during the drilling process;
  circulating the return drilling fluid from the wellbore during the drilling process, the return drilling fluid comprising the drilling fluid, a plurality of cuttings from at least another one of the one or more subterranean formations, and at least one of the another portion of the uniquely identifiable particles;
  separating the drilling fluid from the plurality of cuttings from the another one of the one or more subterranean formations and the at least one of the another portion of the uniquely identifiable particles;
  capturing at least another image of the separated plurality of cuttings and the at least one of the another portion of the uniquely identifiable particles; and
  determining, based on the another image, a depth of the at least another one of the one or more subterranean formations.

18. The method of claim 10, wherein determining, based on the image, the depth of the at least one of the one or more subterranean formations comprises:
  determining, based on the image, the depth of the at least one of the one or more subterranean formations with an artificial intelligence controller that comprises at least one neural network.

19. A computer-implemented method for determining a depth of a subterranean formation, comprising:
  operating, with one or more hardware processors, a camera to capture a first plurality of images of a mixture of cuttings from a first subterranean formation and fluorescent nanoparticles attached to the cuttings from the first subterranean formation within a drilling fluid returned from a wellbore during a drilling process;

determining, with the one or more hardware processors, a particular fluorescent spectra unique to the fluorescent nanoparticles attached to the cuttings from the first subterranean formation based on the first plurality of images;

determining, with the one or more hardware processors, an arrival time of the fluorescent nanoparticles attached to the cuttings from the first subterranean formation at a drill bit of the drilling process;

determining, with the one or more hardware processors, a depth of the drill bit at the determined arrival time;

based on the determined arrival time and depth of the drill bit, determining a depth of the first subterranean formation below a terranean surface;

determining, with the one or more hardware processors, a travel time of the fluorescent nanoparticles attached to the cuttings from the first subterranean formation from a release time to the arrival time of the fluorescent nanoparticles attached to the cuttings from the first subterranean formation at the drill bit; and calculating, with the one or more hardware processors, the travel time based at least in part on a flow rate of the drilling fluid in the drilling process and one or more dimensions of the wellbore.

20. The computer-implemented method of claim 19, further comprising:

operating, with one or more hardware processors, the camera to capture a second plurality of images of a mixture of cuttings from a second subterranean formation and fluorescent nanoparticles attached to the cuttings within the drilling fluid returned from the wellbore during the drilling process;

determining, with the one or more hardware processors, a particular fluorescent spectra unique to the fluorescent nanoparticles attached to the cuttings from the second subterranean formation that is different than the particular fluorescent spectra unique to the fluorescent nanoparticles attached to the cuttings from the first subterranean formation based on the second plurality of images;

determining, with the one or more hardware processors, another arrival time of the fluorescent nanoparticles attached to the cuttings from the second subterranean formation at the drill bit;

determining, with the one or more hardware processors, another depth of the drill bit at the determined another arrival time; and based on the determined another arrival time and the another depth of the drill bit, determining a depth of the second subterranean formation below the terranean surface.

21. The computer-implemented method of claim 19, further comprising:

distinguishing, with the one or more hardware processors, the cuttings from the first subterranean formation and the cuttings from the second subterranean formation based on a difference between the particular fluorescent spectra unique to the fluorescent nanoparticles attached to the cuttings from the first subterranean formation and the particular fluorescent spectra unique to the fluorescent nanoparticles attached to the cuttings from the second subterranean formation.

22. A drilling system, comprising:

a drilling fluid sub-assembly that comprises one or more drilling fluid pumps configured to circulate a drilling fluid into a wellbore during a drilling process to form the wellbore in one or more subterranean formations;

a cuttings collection sub-assembly configured to collect a plurality of cuttings from the subterranean formation from the drilling fluid circulated from the wellbore during the drilling process;

a tagging sub-assembly that comprises a plurality of containers, each of the containers configured to enclose a plurality of uniquely identifiable particles; and a control system communicably coupled to the cuttings collection sub-assembly and the tagging sub-assembly and configured to perform operations comprising:

controlling the tagging sub-assembly to circulate a portion of the plurality of uniquely identifiable particles from one of the plurality of containers into the drilling fluid during the drilling process;

identifying at least one image from an image capture device of the cuttings collection sub-assembly, the image comprising a portion of cuttings from at least one of the one or more subterranean formations and at least one of the portion of the plurality of uniquely identifiable particles from one of the plurality of containers circulated into the drilling fluid during the drilling process;

determining an expected amount of the portion of the plurality of uniquely identifiable particles based at least in part on one or more parameters of the drilling process; and determining, based on the image, a depth of the at least one of the one or more subterranean formations.

23. The drilling system of claim 22, wherein the cuttings collection sub-assembly comprises a shaker assembly configured to receive a mixture of the drilling fluid circulated from the wellbore during the drilling process, the portion of cuttings from at least one of the one or more subterranean formations, and the at least one of the portion of the plurality of uniquely identifiable particles from one of the plurality of containers and separate the drilling fluid from the portion of cuttings and the at least one of the portion of the plurality of uniquely identifiable particles.

24. The drilling system of claim 22, wherein each plurality of uniquely identifiable particles comprise a plurality of uniquely identifiable nanoparticles, each plurality of uniquely identifiable nanoparticles comprising a unique fluorescent spectra.

25. The drilling system of claim 22, wherein the operation of controlling the tagging sub-assembly to circulate the portion of the plurality of uniquely identifiable particles from one of the plurality of containers into the drilling fluid during the drilling process comprises:

controlling a valve of the one of the plurality of containers to adjust toward or to an open position to circulate the portion of the plurality of uniquely identifiable particles from the one of the plurality of containers into the drilling fluid during the drilling process.

* * * * *